US012016664B2

(12) United States Patent
Pekander

(10) Patent No.: US 12,016,664 B2
(45) Date of Patent: Jun. 25, 2024

(54) SYSTEM AND METHOD FOR CONTROLLING A VALVE OF A PORTABLE MEDICAL DEVICE

(71) Applicant: General Electric Company, Schenectady, NY (US)

(72) Inventor: Otto Valtteri Pekander, Helsinki (FI)

(73) Assignee: General Electric Company, Schenectady, NY (US)

(*) Notice: Subject to any disclaimer, the term of this patent is extended or adjusted under 35 U.S.C. 154(b) by 119 days.

(21) Appl. No.: 17/352,052

(22) Filed: Jun. 18, 2021

(65) Prior Publication Data

US 2021/0307620 A1 Oct. 7, 2021

Related U.S. Application Data

(63) Continuation of application No. 15/566,859, filed as application No. PCT/US2016/028251 on Apr. 19, 2016, now Pat. No. 11,045,099.

(30) Foreign Application Priority Data

Apr. 21, 2015 (GB) .................................. 1506738

(51) Int. Cl.
*A61B 5/0225* (2006.01)
*A61B 5/022* (2006.01)
(Continued)

(52) U.S. Cl.
CPC ........ *A61B 5/0235* (2013.01); *A61B 5/02233* (2013.01); *A61B 5/0225* (2013.01);
(Continued)

(58) Field of Classification Search
CPC . A61B 5/0235; A61B 5/02233; A61B 5/0225; A61B 2560/0209;
(Continued)

(56) References Cited

U.S. PATENT DOCUMENTS 4,464,123 A * 8/1984 Glover ................... G09B 23/28
600/494
2007/0239042 A1 10/2007 Takahashi
(Continued)

FOREIGN PATENT DOCUMENTS

CN 202288271 U 7/2012

OTHER PUBLICATIONS

Machine translation and First Office Action and Search issued in connection with corresponding CN Application No. 201680023235.X dated Sep. 20, 2018, 20 pages.
(Continued)

*Primary Examiner* — Rene T Towa
(74) *Attorney, Agent, or Firm* — Andrus Intellectual Property Law, LLP

(57) ABSTRACT

A non-invasive blood pressure monitoring device includes an inflatable blood pressure cuff, a pump device for pressurizing the cuff, a pressure sensor to monitor blood pressure as physiological parameter, and an electrically actuated, normally-open solenoid valve configured to maintain a cuff pressure. A control unit configured to regulate a valve hold value for holding the normally-open solenoid valve at a desired closed position, wherein the valve hold value is at least one of a voltage value and a current value for controlling actuation of the normally-open solenoid valve. At least one inertial sensor configured to detect and transmit motion signals representative of external motions applied to the portable medical device, wherein the control unit is configured to regulate the valve hold value as a function of the motion signals of the at least one inertial sensor to maintain the normally-open solenoid valve in the closed position.

19 Claims, 5 Drawing Sheets

(51) Int. Cl.
*A61B 5/0235* (2006.01)
*A61M 5/142* (2006.01)

(52) U.S. Cl.
CPC . *A61M 5/14244* (2013.01); *A61B 2560/0209* (2013.01); *A61B 2560/0214* (2013.01); *A61B 2562/0219* (2013.01); *A61M 2205/18* (2013.01); *A61M 2205/332* (2013.01); *A61M 2205/505* (2013.01); *A61M 2205/8206* (2013.01)

(58) Field of Classification Search
CPC ... A61B 2560/0214; A61B 2562/0219; A61M 5/14244; A61M 2205/18; A61M 2205/332; A61M 2205/505; A61M 2205/8206; A61M 39/22
See application file for complete search history.

(56) References Cited

U.S. PATENT DOCUMENTS

| | | | |
|---|---|---|---|
| 2008/0281211 A1 | 11/2008 | Whitaker et al. | |
| 2009/0015980 A1* | 1/2009 | Fukano | F16K 31/0675 |
| | | | 361/194 |
| 2009/0156946 A1* | 6/2009 | Lane | A61B 5/02225 |
| | | | 600/490 |
| 2010/0100038 A1 | 4/2010 | Walker et al. | |
| 2010/0137828 A1 | 6/2010 | Michard et al. | |
| 2011/0066050 A1 | 3/2011 | Moon et al. | |
| 2011/0112423 A1 | 5/2011 | Chapman et al. | |
| 2011/0160597 A1 | 6/2011 | Lane et al. | |
| 2012/0059267 A1 | 3/2012 | Lamego et al. | |
| 2012/0065561 A1* | 3/2012 | Ballas | A61H 9/0092 |
| | | | 601/152 |
| 2012/0068096 A1 | 3/2012 | Herbert et al. | |

OTHER PUBLICATIONS

Extended European Search Report and Opinion issued in connection with corresponding EP Application No. 16783677.4 dated Dec. 4, 2018, 8 pages.
International Search Report and Written Opinion for PCT/US2016/028251, dated Jul. 21, 2016, 9 pages.
Combined Search and Exam Report for corresponding GB Appln. No. 1506738.2, dated Oct. 1, 2015, 5 pages.

* cited by examiner

SYSTEM AND METHOD FOR CONTROLLING A VALVE OF A PORTABLE MEDICAL DEVICE

CROSS-REFERENCE TO RELATED APPLICATIONS

This application is a continuation of U.S. patent application Ser. No. 15/566,859, filed Oct. 16, 2017, which is a filing under 35 U.S.C. 371 of international application number PCT/US2016/028251, filed Apr. 19, 2016, which claims priority to Great Britain application number 1506738.2, filed Apr. 21, 2015, the entire disclosures of both are hereby incorporated by reference.

TECHNICAL FIELD

The present disclosure relates to the field of portable medical devices and methods for controlling a valve of a portable medical device. More particularly, the present disclosure relates to a device and method for controlling a solenoid valve of a portable medical device.

BACKGROUND

Valves are operable through movement of an integral actuator or valve driver typically in the form of a solenoid. The solenoid portion of a valve is comprised of an electromagnet, which is in form of a coil and a movable plunger. Such valves are commonly used to govern flow of a fluid or gas. This valve technique is widely utilized within healthcare applications such as portable medical devices, in order to control precisely liquid or gas flow in medical equipment.

Portable medical devices with electrically actuated valves allow medical staff to measure a patient's medical state or supply the patient with a medicament or other required substances. Portable medical devices designed as monitoring device may measure patient vital signs and other parameters including blood pressure or blood sugar. Blood pressure monitoring is one of the principal vital signs. A portable medical devices suited for home health monitoring is for example a non-invasive blood pressure (NIBP) monitoring device. Known non-invasive blood pressure (NIBP) monitoring devices may operate automatically and usually comprise an inflatable cuff, which is wrapped around an arm of a person. To inflate the cuff an air pump may be driven manually or by an electric motor. After inflation a valve is used to bleed the cuff under control in order to measure the blood pressure of the person.

There is a drawback that the battery lifetimes of portable medical devices are not sufficient. Traditional solenoid valves used in non-invasive blood monitoring (NIBP) devices consume over 500 mW constant power, while applying the hold voltage. Hence, there is the need to decrease this power consumption significantly in order to prolong battery lifetimes.

Another problem related to non-invasive blood pressure (NIBP) monitoring devices is that there may be a significant source for disturbing accurate measurements. Since NIBP is indirectly measured based on the change of cuff pressure, it can be affected by motion artifacts much more than other biosignals. Motion artifacts may result from patient movement or from vehicle movements such as vibrations during emergency transportation. Depending on the strength of external movements applied to the portable medical device, inaccurately high or low readings of a monitoring device may result.

In summary, there is the need to provide an energy saving portable medical device and a method to save power consumption of a valve of a portable medical device. Moreover, motion related errors in measurement signals or inaccuracy in medicament supply should be avoided to ensure the safety of the patient and improve accuracy of portable medical devices.

SUMMARY

In accordance with one or more aspects the present disclosure is directed to a device, a computer program product and a method for controlling a valve of a portable medical device as defined by the independent claims.

In one aspect, the present disclosure is directed to a portable medical device comprising:
a power source;
an electrically actuated valve;
a control unit for regulating at least one of a control voltage and a control current for actuation of the valve; and
at least one inertial sensor for detecting and transmitting motion signals representative of external motions applied to the portable medical device;
wherein the control unit is configured to regulate the at least one of control voltage and control current of the valve as a function of the motion signals of the at least one inertial sensor.

In another aspect of the present disclosure is directed to a method for controlling a valve of a portable medical device, comprising the steps:
providing a power source for applying voltage or current to actuate the valve;
detecting with at least one inertial sensor motion signals representative of external motion of the portable medical device;
receiving the motion signals from the at least one inertial sensor by a control unit; and
regulating by a control unit at least one of a control voltage and a control current of the valve as a function of the motion signals.

In yet another aspect, the present disclosure is directed to a computer program product, which computer program product comprises instructions for carrying out the steps of the method according to the present invention, when said product is executed on a processor. By providing a computer program product a portable medical device can be upgraded such that energy consumption for actuation of the valve can be reduced, while ensuring that the valve is maintained in its current position.

Still other aspects and embodiments are defined by the dependent claims and are discussed in detail below. At least one of the embodiments of the present disclosure provides one or more solutions to the problems and disadvantages with the background art. The solutions in accordance with the present disclosure provide a device, computer program product and method for significantly decreasing the energy consumption of a portable medical device and more particularly of a valve of the portable medical device. Another advantage that may be realized in the practice of some embodiments of the described methods and devices is that correction factors can be provided for minimizing errors in parameters monitored by the portable medical device. Other advantages of the present disclosure will be readily apparent to one skilled in the art from the following description and claims.

BRIEF DESCRIPTION OF THE DRAWINGS

The accompanying figures illustrate exemplary embodiments of the disclosure and serve to explain, by way of example the principles of the disclosure and are not intended to be drawn to scale. The figures are included to provide illustration and a further understanding of the various aspects and embodiments, but are not intended to restrict the disclosure to the embodiment illustrated in the figures. Where technical features in the figures or detailed description are followed by references signs, the reference signs have been included for the sole purpose of increasing the intelligibility of the figures and description. For purposes of clarity, not every component may be labeled in every figure.

DETAILED DESCRIPTION

Figure 1:
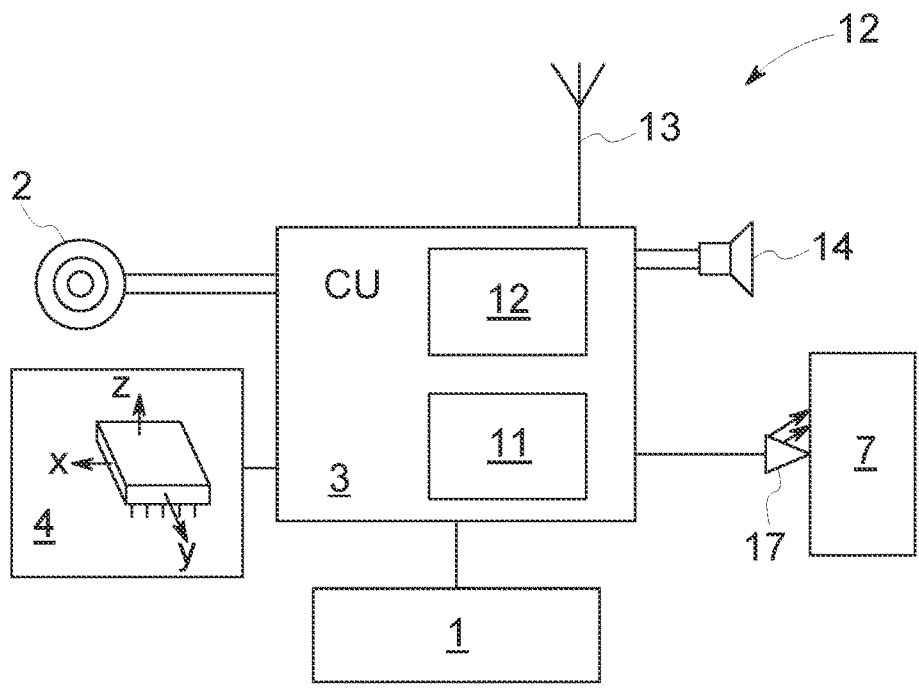
FIG. 1 shows a diagrammatic view of a portable medical device according to an embodiment of the disclosure.

FIG. 1 is a diagrammatic illustration of a portable medical device 10 in accordance with one or more embodiments of the disclosure. The portable medical device 10 comprises a power source 1 and an electrically actuated valve 2. Further it comprises a control unit (CU) 3 for regulating the control voltage or control current for actuation of the valve 2.

The portable medical device 10 can use a plurality of devices to detect external shocks or external motions, which could accidentally change the position of the valve 2. For safety of the patient and accuracy of measurements an unintended change of position of the valve 2 should be avoided. At least one inertial sensor 4 is used for measuring movements as rotation or vibration or any other external movement applied to the portable medical device 10. As shown in FIG. 1 the at least at least one inertial sensor 4 is connected to the control unit (CU) 3. The one or more inertial sensors 4 detect and transmit motion signals to the control unit (CU) 3. Said signals are representative for external motions applied to the portable medical device 10.

One potential embodiment of the inertial sensor 4 is an accelerometer 5. Alternatively, or in addition to the accelerometer 5, a gyroscope may be provided. The at least one inertial sensor is preferably downsized, with advancements of microfabrication technology employing MEMS (Micro-Electro-Mechanical System) techniques. For optimally measuring the influence of vibrations or external shocks to the valve 2, the inertial sensor 4 is disposed in the vicinity of the valve 102. In the vicinity of the valve 102 means that the inertial sensor 104 is not arranged in direct contact with the valve 102 for avoiding measurements of vibrations of the valve itself. In this way the external motions applied to the valve 102 and the portable medical device 100 can be measured as precisely as possible.

The control unit (CU) 3 is configured to regulate the hold voltage and corresponding control output signals as a function of the sensed motion signals. The control unit (CU) 3 can be designed as simple as possible in order to save energy. One possible configuration of the control unit 3 is an analogue circuit 11. In addition or as alternative a processor 12 can be used for regulation. The analogue circuit 11 or processor 12 is used for regulating the voltage or current of the valve 2. One advantage of using only an analogue circuit 11, is that there is a fast response and generation of output signals if a motion is sensed by the inertial senor 4.

The control circuit 11 or processor 12 may be configured, that if no external motions are detected, the control output signals of the control unit (CU) 3 are set to a save minimum voltage. That is to say only after detecting shocks or vibrations by the one or more inertial sensor 4, the valve hold voltage is increased to keep the valve in its current state. If no external motion or stress is detected, the hold voltage or current will be set to a safe minimum, so that power can be saved. In this way the hold voltage of valve 2 can be minimized, when no external motion is measured. This results in a reduction of power consumption.

Based on the motion dependent method for controlling the hold voltage or current of the valve 2 the lifetime of a power source 1 as a battery can be prolonged. In other words the portable medical device 10 is configured to save power, such that a relatively small power source 1 as a battery or a rechargeable accumulator can be used.

The portable medical device 10 of FIG. 1 further comprises a display 7. The display 7 has a backlight using LEDs 17. LEDs 17 have the advantage that they have a low energy consumption. If the valve 2 is used for applications as for example for dosing a medicine or an infusion liquid the display can indicate the flow rate or dose regulated by the portable medical device 10. The flow rate may be measured by a suitable sensor (not shown) or received wireless via the communication unit 13. Depending on the application other data as monitored parameters can be displayed by the display 7. Optional such monitoring data or any other status data can be sent from the control unit (CU) 3 via the communication unit 13 to another device as a phone or watch and the like.

Further the portable medical device 10 may comprise a loud speaker 14. If the motion measured by the inertial sensor 4 exceeds a predetermined threshold the loud speaker 14 is actuated by the control unit to give a warning signal. In this way the user of the control device can be warned that significant shocks have been applied to the medical device.

According to a preferred embodiment of the disclosure the valve 2 is a solenoid valve 2 as indicated schematically by the concentric circles in FIG. 1. As is well known, a solenoid is essentially a coil of wire or winding that is wrapped around a hollow bobbin. The solenoid valve device is actuated by an electrical control current or control voltage, which generates a magnetic field to bias a plunger within a valve body (not shown) between a first, open position to a second, closed position to control a liquid flow or gas flow. Besides the described plunger-type actuator other suitable actuators can be used. In the case of a two-port valve a flow can be switched on or off. If such a two port valve is open when the solenoid is not energized, then the valve is termed normally open. Depending on the application either normally open or normally closed valves are preferred. Potential tasks of the solenoid valve 2 of the portable medical device 10 can be to shut off, release or dose medicaments or other fluids.

Figure 2:
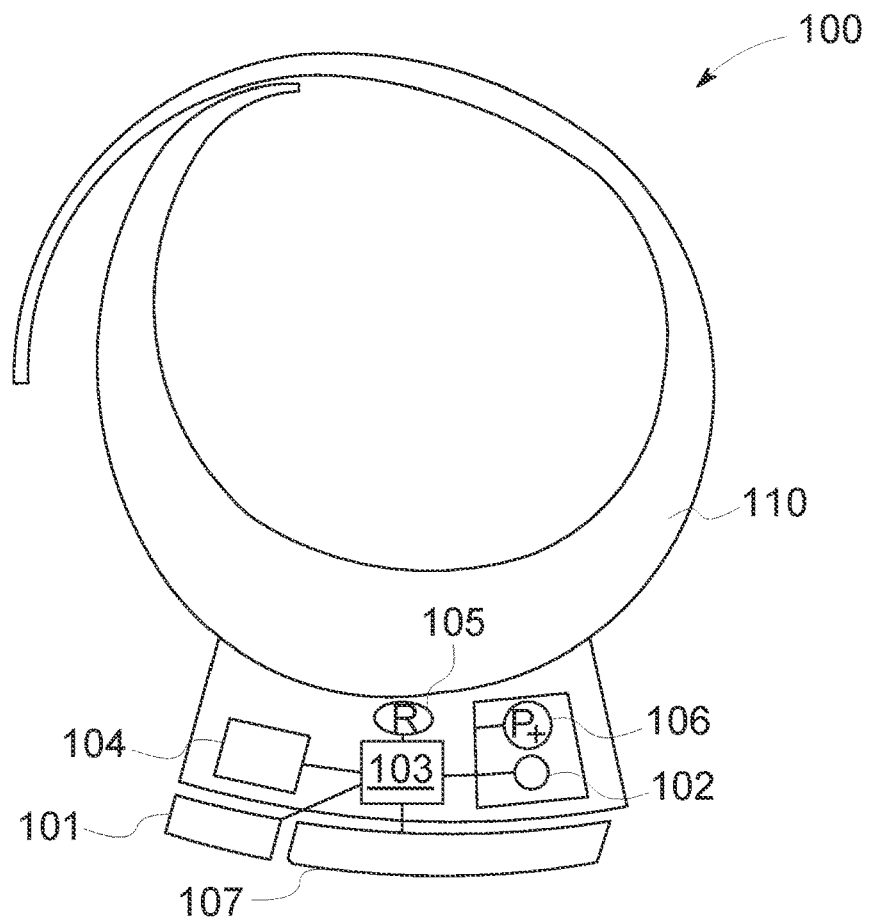
FIG. 2 shows a diagrammatic illustration of a portable medical device configured as a non-invasive blood monitoring (NIBP) device according to another embodiment of the disclosure.

According to one or more aspects of the present disclosure the portable medical device 100 is a non-invasive blood (NIBP) monitoring device as schematically shown in FIG. 2. If the valve hold voltage is not actively modulated as according to the present disclosure, but only a constant maximum hold voltage is used, it was found that the valves of NIBPs are presenting over 50% of the total power consumption of the NIBP measurement. However, by modulating the hold voltage according to the present disclosure i.e. based on the measured motion signals, the battery time can be doubled if normal situations without external motion are assumed. According to this energy saving method a NIBP monitoring device can operate at least 36 hours without charging.

FIG. 2 is schematically illustrating a portable medical device 100, which is configured as a non-invasive blood pressure (NIBP) monitoring device. The cuff 110 can be attached to a limb of a person, typically around the upper or lower part of a person's arm. In a clinical environment, there is a range of cuff sizes available to accommodate different limb sizes or different ages of a patient. The blood pressure cuff 110 comprises a bladder (not shown), which can be inflated to a pressure above the highest expected systolic blood pressure. During the inflation, the valve 102 is in a closed position. The inflation of the cuff 110 is performed automatically by the pump 106. Alternatively, the inflation of the cuff can be performed manually.

After an inflation, the valve 104 can be opened and the pressure of the bladder monitored by the pressure sensor 105. The pressure sensor 105 generates an analogue or digital pressure output signal as the bladder inflates or deflates. The pressure sensor 105 can detect oscillatory pressures that occur within the inflated cuff. In this way blood pressure parameters, such as the systolic pressure or diastolic pressure, can be calculated from the detected pressure signals and displayed by the display 107. The display 107 can be an LCD display or any other suited display.

The non-invasive blood pressure (NIBP) monitoring device includes a control unit 103 comprising a processor to analyze the pressure signals measured by the pressure sensor 105. Moreover the control unit 103 is used to regulate the hold voltage or the valve 104. The electronic components of the portable medical device 100 as the valve 102 or the display 107 are powered by a power source 101, which can easily be replaced for recharging by the user.

In order to save power in response to any external motions to the portable medical device 100 comprises at least one inertial sensor 104. The at least one inertial sensor 104 is configured as an accelerometer or a gyroscope, and can accurately sense the motions applied to the control device 100. If external motions are sensed by the inertial sensor 104 the valve 102 can be regulated accordingly. The valve 102 can be regulated by modulating either the control voltage or the control current for actuation of the valve. For accurate measurements of the blood pressure 105 it is important to safely maintain the valve closed.

If a detected rate of change in motion is only representing small vibrations the valve 104 can be reliably closed with less hold voltage than in a case, when a significant rate of change is detected as after a shock. In other words the control current or control voltage is increased in dependence of the intensity of the external motion detected by the inertial sensor 104. In this way the voltage needed for reliably holding the valve 104 can be actively regulated and thereby power can be saved.

Figure 3:
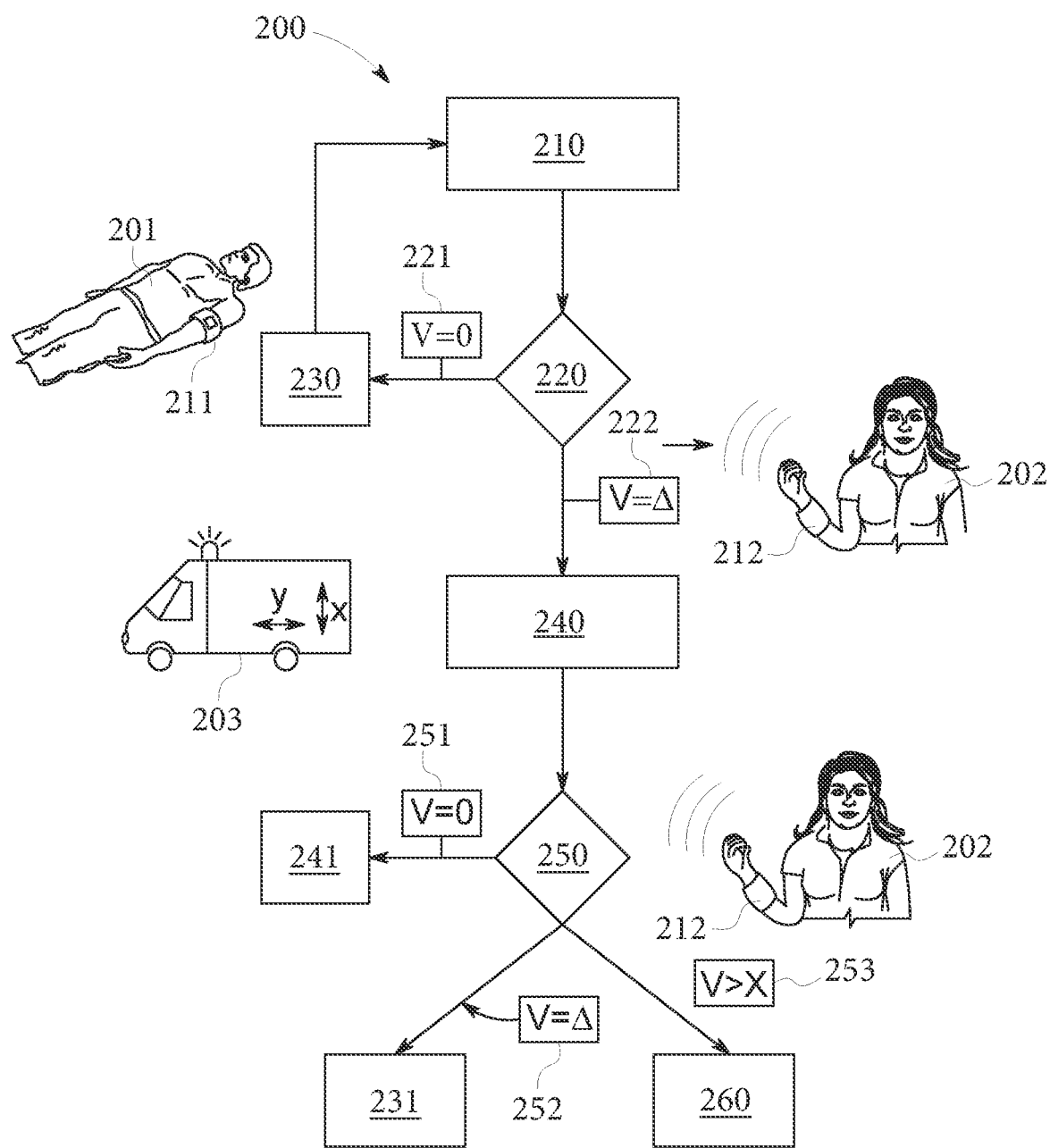
FIG. 3 shows a diagrammatic flow chart of a method for controlling a valve according to an embodiment of the disclosure.

According to another aspect of the present disclosure, a method is provided. FIG. 3 shows schematically a flow chart of a method 200 for controlling a valve of a portable medical device according to one or more embodiments of the present disclosure.

The method for controlling a valve 200 starts with the step 210, wherein a power source is provided for applying voltage or current to actuate a valve. If the portable medical device 211, 212 is a non-invasive blood pressure (NIBP) monitoring device, which can be wrapped around the arm of a person 201, 202 as cuff, the valve is a normally open solenoid valve. Said valve is operated in step 210 such, that it is in a closed position after actuation. The solenoid valve of the NIBP monitoring device is actuated by an electrical control current or control voltage, which generates a magnetic field to bias a plunger of the valve between the first, open position to a second, closed position.

In step 220 motion signals are detected by the at least one inertial sensor 4 of the portable medical device. The motion signals can, for example, be caused by movements of an ambulance, in which a patient 201 may be transported in a lying, or supine, position. On the other hand the motion signals can be the result of movements of the person 202 such as shivering, which is schematically indicated by the arrow and plurality of partial circles besides the person 202. The motion signals sensed by the inertial sensor comprise a rate of change in motion and are received by a control unit (method step 221). If the inertial sensor has detected a rate of change in motion, which is zero (V=0) as indicated in step 221, the control unit of the portable medical device generates a first valve control signal, to regulate a valve hold circuit at a minimum valve hold value (step 230). Accordingly, if no motion is detected by the inertial sensor, power can be reduced to the lowest value possible, such that the holding of the valve is still safely ensured.

In case of external motions, such as vibrations or shocks, a rate of change is detected as indicated in step 222 (V=Δ). Then the control unit generates a second valve control signal, to regulate the valve hold value based on the detected rate of change (step 240). That is to say the control unit is configured to generate valve control signals that increase the control voltage or control current for holding the valve, such that the valve reliably stays closed.

Step 250 is comparable to step 220 since the motion signals are detected by the at least one inertial sensor 4 and based on the detected motion signals, the control unit generates different output signals. If the patient or person 201, 202, who wears the portable medical device 211 or 212, is passively moved or unintentionally actively moves the portable medical device, the same rate of change in motion is detected in step 252 (V=Δ). In this case, the holding voltage or current is regulated such that the current status of the valve is maintained in method step 231. If lower or higher rates of change are detected, the holding voltage may be modulated such that the closure of the valve is ensured.

If there is no motion applied to the portable medical device and V=0 detected in step 251, the current or voltage for holding the valve in the desired position is reduced to the minimum voltage in method step 241. In this situation, the method can start from the beginning i.e. at step 210, wherein the valve is in a normal actuated state with minimum voltage for holding the valve position.

According to another embodiment of the present disclosure, the portable medical device comprises a timer and corresponding method steps are provided, which is schematically illustrated in method step 260. Accordingly the control unit is configured to generate third valve control signals, when the detected rate of change in motion exceeds a predetermined hold value X. Based on the third valve control signals, the valve hold circuit is increased to ensure the current position of the valve and maintains the required hold voltage for a predetermined time. In this way it can be ensured that for a specific time period an increased hold voltage is applied. This can be of advantage, for example, if the person 201 is transported in an ambulance 203. After the beginning of driving motions, further motions can be expected. After the predetermined time period has passed, the method returns to the beginning to the method step 210 and if no more external motions are sensed, the valve is held in its current position with the required minimum voltage or current.

According to another embodiment of the present disclosure, the method may not only monitor a physiological parameter, but also a parameter of a medicament and a parameter of the delivery of a dosing medium by a monitoring device. In a preferred embodiment, the monitored parameters of the monitoring device can be corrected based on motion signals of the inertial sensor. Alternatively the monitored parameters of the monitoring device can be corrected based on variations from characteristic statistical values of the monitoring device to minimize motion induced errors. In this way the accuracy of a monitoring device such as a NIBP monitoring device can be maintained, even if motions are applied to the portable medical device.

Figure 4:
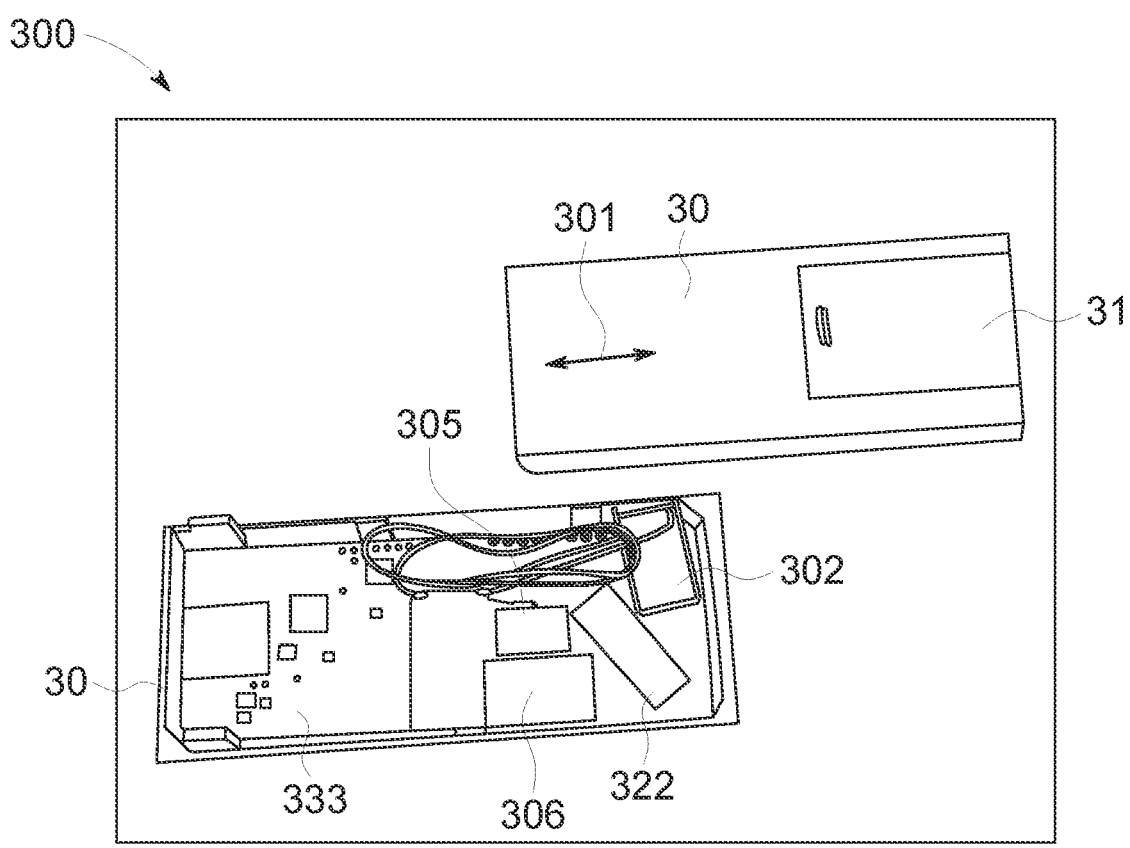
FIG. 4 shows a diagrammatic illustration of a portable medical device according to another embodiment of the disclosure.

FIG. 4 shows diagrammatically another embodiment of a portable medical device 300, which is designed as a non-invasive blood pressure (NIBP) monitoring device. The portable medical device 300 is arranged in a housing 30. The housing 30 has a movable part 31 which can be moved in order to clear a space for a power source, which is not shown in FIG. 4. The relative small size of the portable medical device 300 is indicated by the double arrow 301, which corresponds approximately to the diameter of an 1 EURO coin (approximately 2-3 cm).

The housing 30 shown in the lower part of FIG. 4 comprises a circuit board 333 with a control unit (CU). Said control unit (CU) can, for example, comprise a analogue circuit and/or a microprocessor. Further a pump device 306 and the valves 302 and 322 are arranged in the housing. An inertial sensor 305 is arranged in the vicinity of the valve. Both parts of the housing 30 are assembled as one housing 30. The following FIG. 5 shows an assembled housing 30, which is arranged on a cuff 310.

Figure 5:
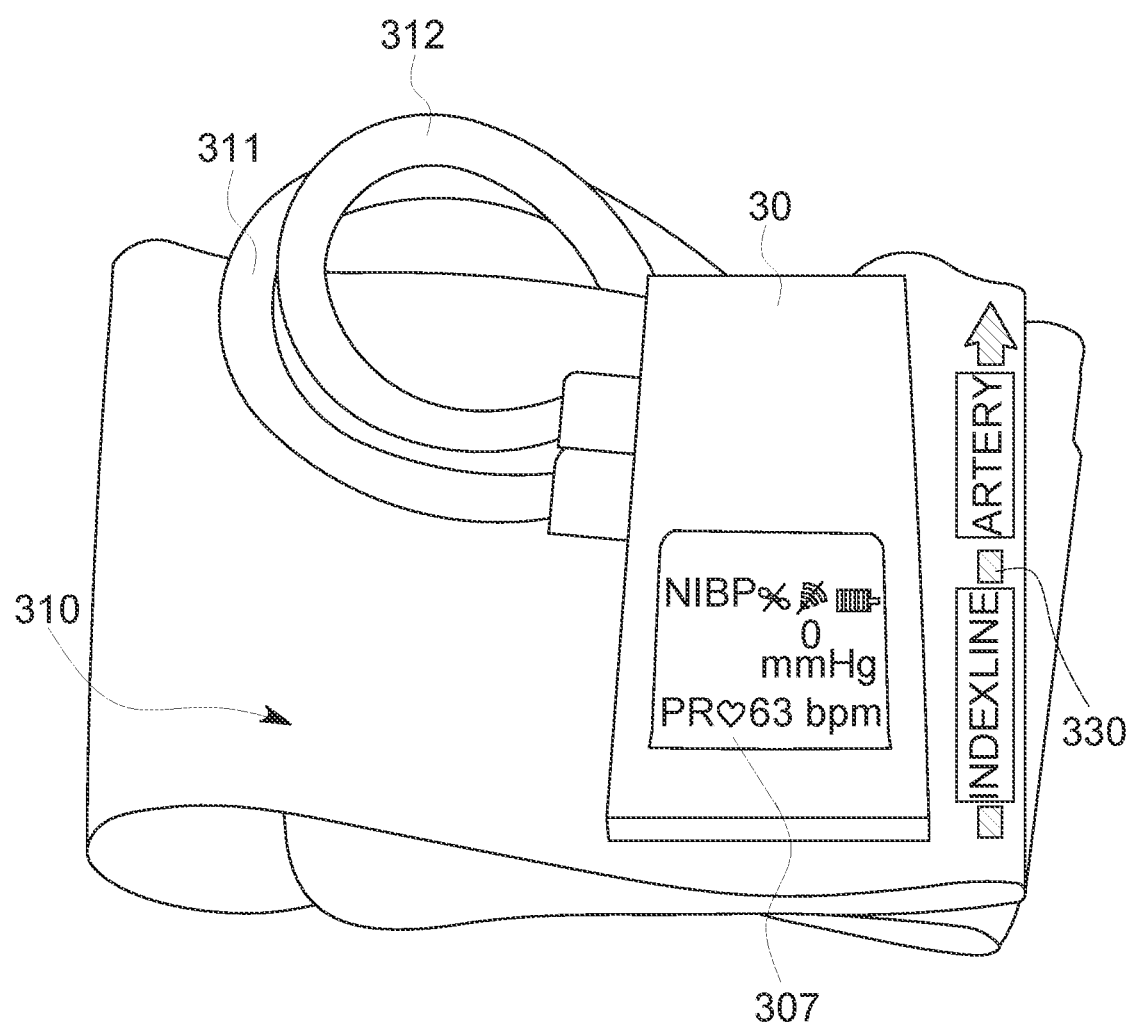
FIG. 5 shows a diagrammatic illustration of a portable medical device configured as a non-invasive blood pressure monitoring device according to another embodiment of the disclosure.

FIG. 5 shows the housing 30 of FIG. 4 with a display 307 for indicating the measured blood pressure (NIBP) of a patient or person. The cuff 310 of the portable medical device can be wrapped around an extremity of a person. When positioning the cuff 310 on the patient it must be ensured that the artery index line is aligned with the artery of the lower or upper arm, to provide accurate blood pressure monitoring. FIG. 5 further shows at the side of the housing first and second cuff hoses 311, 312 which are connected to the first and second valves 302, 322 in the housing. The cuff 310 can be inflated via the pump 306 (see FIG. 4).

A plurality of physiological parameters can be shown in the display 307. FIG. 5 shows for example the NIBP in mmHg measured by a pressure sensor. Further a pressure signal processor is used for computing other parameters of interest such as the heart rate in beats per minute (bpm). Further the battery charging status can be displayed.

According to a preferred embodiment of the present disclosure a pressure signal processor of the portable medical device 300 can use an algorithm for correcting the monitored parameters based on the motion signals of the at least one inertial sensor 305. In this way motion induced errors of the blood pressure can be minimized and accuracy of measurements improved.

Alternatively or in addition to the motion based correction, the pressure signal processor can use an algorithm for correcting the blood pressure using the monitored pressure data. In order to be able to compare significant changes in pressure as spikes, first normal pressure variations without the impact of external movements have to be recorded in a memory. Such historical data can be collected for each patient by statistical analysis and recorded in the memory. If the pressure exceeds a predetermined threshold value, the processor can determine that movement has occurred and the pressure data may be corrected accordingly. Based on said analysis and detection of pressure spikes, it is also possible that the voltage or current of the valve is increased.

Figure 6:
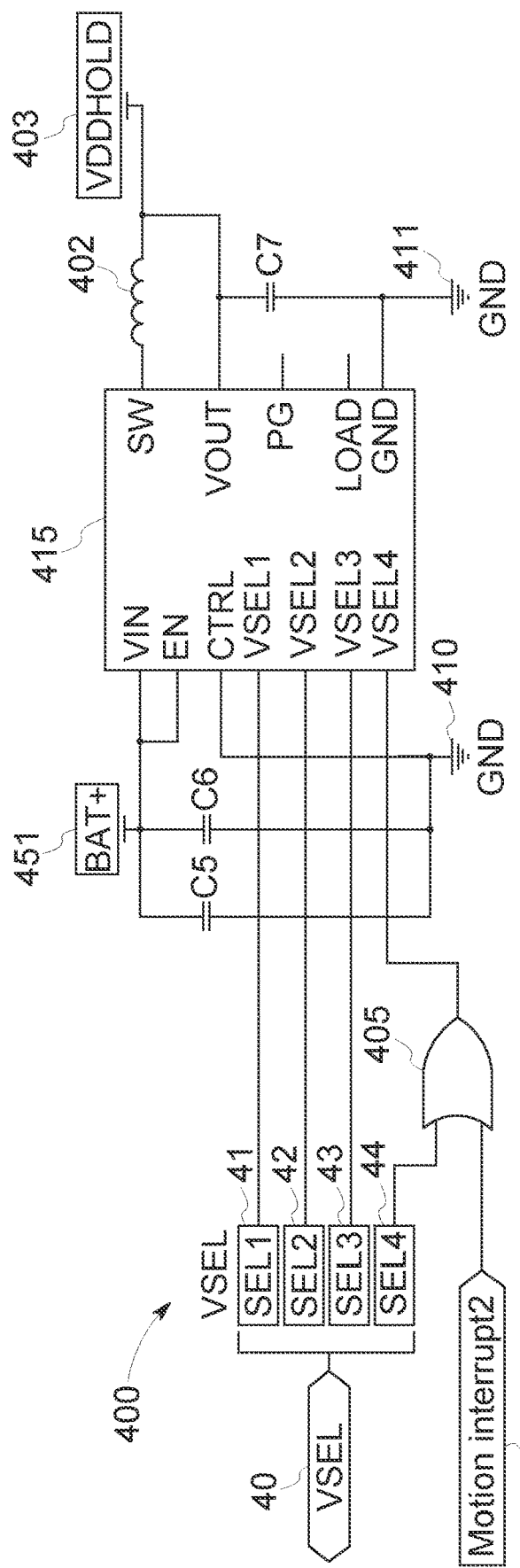
FIG. 6 presents a schematic diagram of a control circuit in accordance with one or more embodiments of the disclosure.

FIG. 6 shows a schematic diagram of a control unit designed as a control circuit 400 according to one or more embodiment of the present disclosure. The input signals come in from the left side of the control circuit 400 i.e. from the VSEL (see hexagon 40) or "Motion interrupt 2". VSEL comprises selected input values SEL1 to SEL4, wherein each line 41, 42, 43 and 44 is connected to the Power management integrated circuit (PMIC) 415. The PMIC 415 controls the flow and amount of electrical power of the portable medical device and more particularly regulates the voltage. PMIC 415 sets the predetermined output voltage values VOUT in dependence of the monitored motion signals. The output voltage VOUT may be for example ranging from minimum 1.8 Volt to maximum 3.3 Volt. In normal situations without any external motions the lowest necessary voltage value is outputted at VOUT corresponding to for example 1.8 Volt.

For supplying the hold voltage via the PMIC 415 to the valve the control circuit 400 comprises a power source 451, which can be designed as a rechargeable battery. Further, a plurality of capacitors as an input capacitor C6 or an output capacitor C7 is provided.

In order to accelerate the response in case of significant motion shocks to the portable medical device the so called "Motion interrupt2" comes directly from an inertial sensor and via the gate 405 to the PMIC 415. In case of a significant motion signal representing a shock the PMIC 415 forces the output voltage VOUT to be high. In this way the voltage to hold the valve "VDDHOLD, 403" can be set to a predetermined value. This may imply an increase from an initial 1.8 Volt to a voltage value of 2.6 Volt.

According to an embodiment of the disclosure, the control unit for voltage drive of the valve may not only comprise the control circuit but also a processor. The processor gives more flexibility for the modulating or regulating the holding voltage 403 of the valve 402. The processor may control based on motion signals, that a shock is over and no other movement is detected. Then the valve can be controlled by setting VSEL 1 to 3 as zero. The processor clears the motion interrupt from the accelerometer and the voltage decreases back to the initial voltage, which may be 1.8 Volt.

If alternatively a movement is still detected and a motion interrupt is outputted by the gate 405, then the processor may set all lines (VSEL 1-4) to high. The driving voltage regulated by PMIC 415 would rise further to 3.3 Volt and stay there until an algorithm on the processor determines that the movement is over. Then the voltage can gradually be reduced back to the minimum, which is in the above example 1.8 Volt. There are different ways and voltages ranges to regulate the driving voltage or current of the valve and the above example is not limiting.

This written description uses examples to disclose the invention, including the best mode, and also to enable any person skilled in the art to practice the invention. This includes making and using any devices and performing any incorporated methods. The patentable scope of the invention is defined by the claims, and may include other examples that occur to those skilled in the art.

I claim:

1. A non-invasive blood pressure monitoring device comprising:
   an inflatable blood pressure cuff;
   a pump device for pressurizing the blood pressure cuff;
   a pressure sensor to monitor blood pressure as physiological parameter;
   an electrically actuated, normally-open solenoid valve configured to control a cuff pressure by bleeding gas from the pressurized cuff;
   a control unit configured to regulate a valve hold value for holding the normally-open solenoid valve at a closed position during a measurement period, wherein the valve hold value is at least one of a voltage value and a current value for controlling actuation of the normally-open solenoid valve; and
   at least one inertial sensor configured to detect and transmit motion signals representative of external motions applied to the blood pressure cuff by a patient wearing the blood pressure cuff;
   wherein the control unit is configured to adjust the valve hold value as a function of the motion signals of the at least one inertial sensor to maintain the normally-open solenoid valve in the closed position such that the normally-open solenoid valve is energized to stay closed and maintain the cuff pressure during the measurement period despite motion of the patient.

2. The non-invasive blood pressure monitoring device of claim 1, wherein the motion signals comprise a rate of change in motion.

3. The non-invasive blood pressure monitoring device of claim 2, wherein the control unit is configured to regulate the valve hold value at a constant level for a predetermined time when the rate of change in motion is greater than a predetermined threshold.

4. The non-invasive blood pressure monitoring device of claim 2, wherein the control unit is configured to generate a motion warning when the rate of change in motion exceeds a predetermined threshold.

5. The non-invasive blood pressure monitoring device of claim 1, wherein the at least one inertial sensor is disposed in a vicinity of the valve but not in direct contact with the valve.

6. The non-invasive blood pressure monitoring device of claim 1, wherein the at least one inertial sensor comprises at least one of an accelerometer and a gyroscope.

7. The non-invasive blood pressure monitoring device of claim 1, wherein the control unit is further configured to regulate the valve hold value for holding the normally-open solenoid valve at the closed position by increasing the valve hold value when a pressure signal from the pressure sensor exceeds a threshold magnitude based on normal pressure variations for the patient.

8. The non-invasive blood pressure monitoring device of claim 1, wherein based on the motion signals of the at least one inertial sensor the control unit uses an algorithm for correcting the blood pressure to minimize motion induced errors.

9. The non-invasive blood pressure monitoring device of claim 8, wherein the control unit is configured such that a pressure signal is corrected at locations where a magnitude of the pressure signal exceeds a threshold magnitude based on historical pressure data for the patient.

10. The non-invasive blood pressure monitoring device of claim 1, wherein based on variations from characteristic statistical pressure values that exceed a threshold value, the control unit uses an algorithm for correcting the blood pressure to minimize motion induced errors.

11. A method for controlling a normally-open solenoid valve of a non-invasive blood pressure monitoring device including a blood pressure cuff, the method comprising:
    detecting, with at least one inertial sensor, motion signals representative of external motion applied to the blood pressure cuff by a patient wearing the blood pressure cuff; and
    adjusting by a control unit a valve hold value as a function of the motion signals to hold the normally-open solenoid valve at a closed position to maintain pressure in the blood pressure cuff during a measurement period, wherein the valve hold value is at least one of a voltage value and a current value for actuation of the normally-open solenoid valve toward the closed position such that the normally-open solenoid valve is energized to stay closed and maintain the cuff pressure during the measurement period despite motion of the patient.

12. The method of claim 11, wherein the motion signals include a rate of change in motion.

13. The method of claim 12, further comprising regulating the valve hold value at a constant level for a predetermined time when the rate of change in motion is greater than a predetermined threshold.

14. The method of claim 12, wherein regulating the valve hold value includes:
    generating a first output control signal by the control unit to regulate the valve hold value at a minimum valve hold value when a detected rate of change in motion is zero; and
    generating a second output control signal by the control unit to regulate the valve hold value at an increased valve hold value that is based on the detected rate of change in motion when the rate of change in motion is greater than zero.

15. The method of claim 14, further comprising generating a third output control signal by the control unit to regulate the valve hold value at the increased valve hold value and maintain the increased valve hold value at a constant level for a predetermined time when the rate of change in motion is greater than zero and exceeds a predetermined threshold value.

16. The method of claim 11, further comprising increasing the valve hold value when at least one of a pressure signal from a pressure sensor in the blood pressure cuff exceeds a threshold magnitude or the motion signal exceeds a predetermined threshold.

17. The method of claim 11, further comprising:
    determining a threshold magnitude based on normal pressure variations for the patient;
    comparing a pressure signal from a pressure in the blood pressure cuff to the threshold magnitude; and
    controlling the valve hold value based further on the comparison.

18. The method of claim 17, further comprising correcting the blood pressure to minimize motion induced errors based on the comparison.

19. The method of claim 18, wherein correcting the blood pressure includes correcting the pressure signal at locations where a magnitude of the pressure signal exceeds a threshold magnitude.

* * * * *